May 30, 1972 J. T. IRWIN Plant Pat. 3,204
KALANCHOE PLANT
Filed Nov. 27, 1970
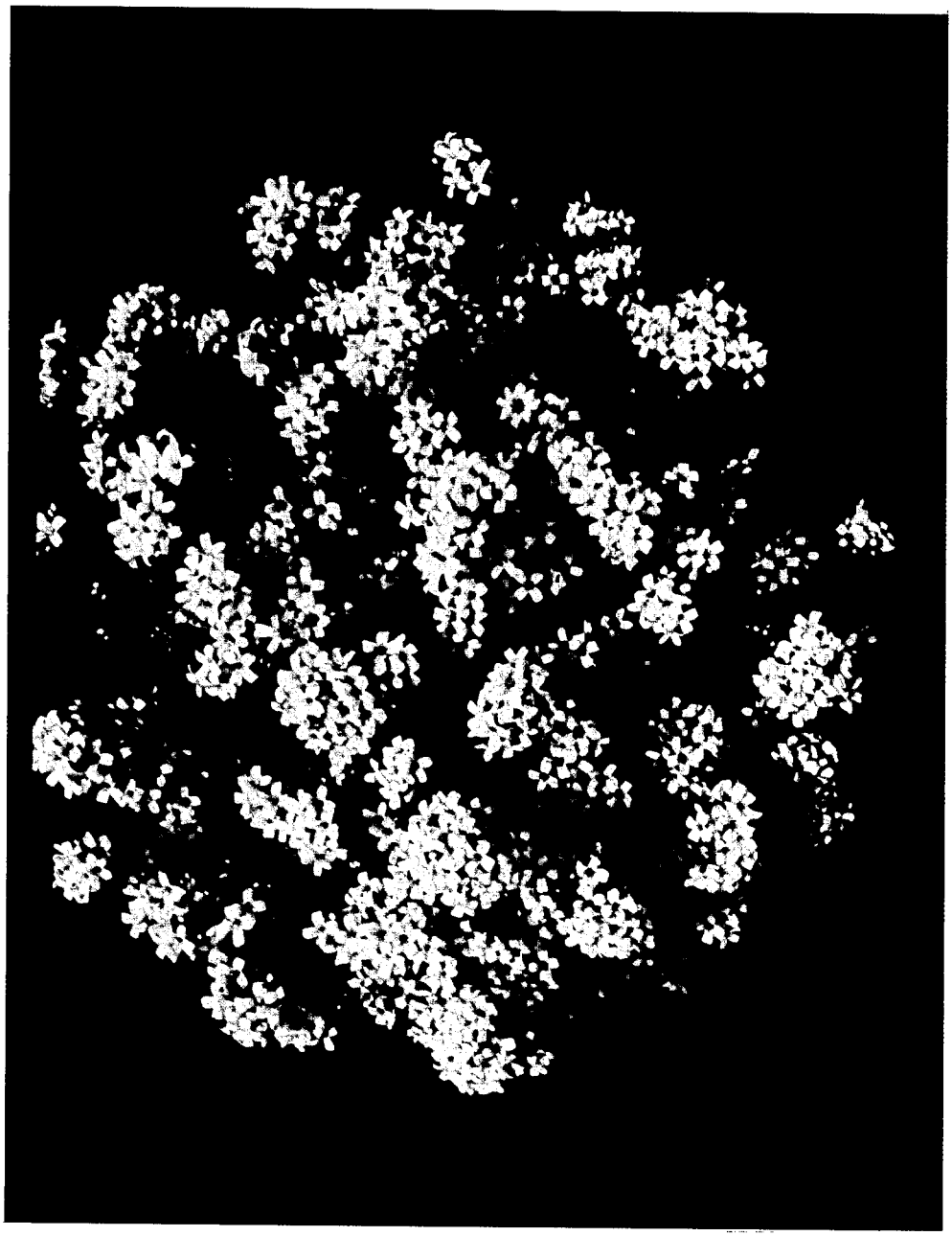
Inventor.
James T. Irwin
By: Robb & Robb
Attorneys.

United States Patent Office

Plant Pat. 3,204
Patented May 30, 1972

3,204

KALANCHOE PLANT

James T. Irwin, Canyon, Tex., assignor to Irwin Greenhouses, Inc., Canyon, Tex.

Filed Nov. 27, 1970, Ser. No. 93,515
Int. Cl. A01h *5/00*
U.S. Cl. Plt.—68 1 Claim

The present invention relates to a new and distinct variety of kalanchoe plant, which was discovered by me on the nursery property of my assignee located in Randall County, Tex., as a selected, cultivated seedling derived from the planting of seeds of the Swiss kalanchoe variety known as "Violacea" (unpatented).

In the course of commercially growing the kalanchoe variety "Violacea," I found that although its flower color was desirable and satisfactory, it was otherwise an unsatisfactory variety particularly because of its tall and thin habit of growth. I, therefore, undertook to improve upon that variety by developing a variety having a more dwarf and compact plant habit, while maintaining the good flower color. This objective was achieved by planting seeds of the "Violacea" variety and from which I selected the present new seedling which I recognized as being superior to "Violacea," as evidenced by the following unique combination of outstanding characteristics which distinguish it from its parent, as well as from all other kalanchoe varieties of which I am aware:

(1) A uniformly dwarf, spreading habit of growth, topped with numerous short-stemmed clusters of flowers;
(2) A highly self-branching and sturdy growing habit;
(3) A uniform blooming habit throughout the year;
(4) A distinctive and attractive rose pink flower color which blends well with the fern green foliage which has a wine colored etching on the reverse surface of the foliage and which is intensified under high light and cool weather conditions;
(5) Long lasting qualities as a potted plant;
(6) An ability to initiate and develop flower buds during high night-time temperatures of summer when other varieties stall; and
(7) An ability to respond to photo-period changes, with consequent suitability for year around flowering.

Asexual reproduction of my new kalanchoe variety by direct rooting of stem tip cuttings, as performed by me in Randall County, Tex., shows that the foregoing characteristics and distinctions come true and are established and transmitted through succeeding propagations.

The accompanying drawing shows a typical specimen blooming plant of the new kalanchoe variety as depicted in color as nearly true as it is reasonably possible to make the same in an illustration of this character.

The following is a detailed description of my new variety, with color terminology in accordance with Exotica Horticultural Color Guide, Roehrs Co., except where general color terms of ordinary dictionary significance are obvious:

Parentage: A selected, cultivated seedling of the Swiss kalanchoe variety known as "Violacea."

Propagation: Holds its distinguishing characteristics through succeeding propagations by direct rooting of stem tip cuttings.

Locality where grown and observed: Randall County, Tex.

Plant:

*Form.*—Bush; medium dwarf (uniformly 10 inches to 12 inches tall); much-branched; compact; spreading.

*Growth habit.*—Sturdy.

*Rooting habit.*—Numerous and fibrous roots; roots easily from any part of stem.

*Blooming habit.*—Compound umbel.

*Blooming season.*—Normally about mid-December, but responds well vegetatively to photo-period changes during long days and also blooms well during short days, with consequent suitability for flowering all year around.

Foliage:

*Size.*—Length—about 2¼ inches. Width—about 1¾ inches.

*Quantity.*—Abundant.

*Color.*—New foliage—Upper side—Green, No. 83+. Under side—Green, No. 83−. Old foliage—Upper side—Green, No. 83. Under side—Green, No. 83−, with tip and marginal etching of Wine color, No. 34, under cool, bright weather conditions.

*Shape.*—Obovate. Tip—obtuse. Base—from acute to obtuse.

*Texture.*—Upper side—glossy; smooth. Under side—smooth.

*Margin.*—Crenate.

Disease resistance: More resistant to root rot than most kalanchoe varieties in present day commercial production, as determined by comparison with other varieties grown under the same greenhouse conditions in Randall County, Tex.

Flowers: Complete; average diameter about 21/32 inch; average depth about 17/32 inch.

*Form.*—Perigynous; 4-parted calyx, corolla and pistil; 8 stamens; section petals united; ovary inferior.

*Color.*—Upper side of petals—Newly open—Rose color No. 38+. Older petals—Rose color No. 38. Under side of petals—Rose color No. 37.

*Blooming period.*—From 3 to 6 weeks.

Hardiness: Withstands temperatures as high as from 105° to 110° F. in greenhouse, and as low as around 40° F.

General observations: The short, compact growth, topped with numerous short flowering stems having hundreds of individual flowers opening over a long period of time, maintains the attractiveness of the plants for 3 to 6 weeks; plants finish best under high light conditions or under a lamp in the home; foliage tends to curl upward and develop a wine colored etching on the under light and cool temperature conditions. While the flower color is much the same as that of "Violacea," the plants of my new variety are much more self-branching and more dwarf in overall growth than "Violacea," especially in respect to flower stem elongation, while capable of maintaining and flowering response throughout the year.

I claim:

1. A new and distinct variety of kalanchoe plant, substantially as herein shown and described, characterized particularly as to novelty by the unique combination of a uniformly dwarf, spreading habit of growth, topped with numerous short-stemmed clusters of flowers, a highly self-branching and sturdy growing habit, a uniform blooming habit throughout the year, a distinctive and attractive rose pin flower color which blends well with the fern green foliage which has a wine colored etching on the reverse surface of the foliage and which is intensified under high light and cool weather conditions, long lasting qualities as a potted plant, an ability to initiate and develop flower buds during high night-time temperatures of summer when other varieties stall, and an ability to respond to photo-period changes, with consequent suitability for year around flowering.

No references cited.

ROBERT E. BAGWILL, Primary Examiner